US012766274B2

(12) United States Patent
Dayioglu

(10) Patent No.: US 12,766,274 B2
(45) Date of Patent: Oct. 20, 2026

(54) INHALER ARTICLE HOLDER WITH ELECTROSTATIC DISCHARGE

(71) Applicant: PHILIP MORRIS PRODUCTS S.A., Neuchâtel (CH)

(72) Inventor: Onur Dayioglu, Neuchâtel (CH)

(73) Assignee: Philip Morris Products S.A., Neuchâtel (CH)

( * ) Notice: Subject to any disclaimer, the term of this patent is extended or adjusted under 35 U.S.C. 154(b) by 748 days.

(21) Appl. No.: 18/038,899

(22) PCT Filed: Dec. 1, 2021

(86) PCT No.: PCT/IB2021/061191
§ 371 (c)(1),
(2) Date: May 25, 2023

(87) PCT Pub. No.: WO2022/123398
PCT Pub. Date: Jun. 16, 2022

(65) Prior Publication Data

US 2024/0207540 A1 Jun. 27, 2024

(30) Foreign Application Priority Data

Dec. 11, 2020 (EP) .................................... 20213327

(51) Int. Cl.
*A61M 15/00* (2006.01)
*A24F 42/20* (2020.01)

(52) U.S. Cl.
CPC .... *A61M 15/0008* (2014.02); *A61M 15/0035* (2014.02); *A61M 15/004* (2014.02);
(Continued)

(58) Field of Classification Search
CPC ..... A24F 40/05; A24F 42/20; A61M 15/0005; A61M 15/0008; A61M 15/003;
(Continued)

(56) References Cited

U.S. PATENT DOCUMENTS

| | | | | |
|---|---|---|---|---|
| 3,888,253 A * | 6/1975 | Watt | A61M 15/0041 128/203.15 |
| 6,092,522 A * | 7/2000 | Calvert | A61M 15/0033 128/203.15 |

(Continued)

FOREIGN PATENT DOCUMENTS

| | | |
|---|---|---|
| EP | 0 613 384 A1 | 9/1994 |
| EP | 3 481 471 A1 | 5/2019 |

(Continued)

OTHER PUBLICATIONS

Japanese Office Action for JP 2023-535377 issued by the Japanese Patent Office on Aug. 12, 2025; 10 pgs. including English Translation.

(Continued)

*Primary Examiner* — Bradley H Philips
(74) *Attorney, Agent, or Firm* — Mueting Raasch Group

(57) ABSTRACT

An inhaler article holder for an inhaler article including a housing defining a housing cavity and an outer surface and a sleeve positioned within the housing cavity. The sleeve is arranged to receive an inhaler article and the sleeve is movable within the housing cavity between a first position and a second position. A piercing element is arranged to pierce the inhaler article received within the sleeve when the sleeve is in the second position. The sleeve is electrically coupled to the housing to form a static electricity discharge circuit when the housing is electrically grounded.

20 Claims, 4 Drawing Sheets

(52) U.S. Cl.
CPC ............ *A24F 42/20* (2020.01); *A61M 15/003* (2014.02); *A61M 2205/0233* (2013.01)

(58) Field of Classification Search
CPC ............ A61M 15/0035; A61M 15/004; A61M 15/0041; A61M 15/06; A61M 2202/064; A61M 2205/0233; A61M 15/0036
See application file for complete search history.

(56) References Cited

U.S. PATENT DOCUMENTS

| | | | | |
|---|---|---|---|---|
| 6,978,915 | B1 * | 12/2005 | Russell | B65D 83/38 222/402.1 |
| 2005/0005929 | A1 * | 1/2005 | Snyder | A61M 15/0086 128/200.23 |
| 2010/0108062 | A1 * | 5/2010 | Ganem | A61M 15/0028 128/203.21 |
| 2011/0277752 | A1 | 11/2011 | Cheu et al. | |
| 2015/0013696 | A1 * | 1/2015 | Plojoux | A24F 40/40 131/328 |
| 2016/0151589 | A1 | 6/2016 | Ohrt et al. | |
| 2017/0135397 | A1 | 5/2017 | Buehler et al. | |
| 2019/0116879 | A1 * | 4/2019 | Zuber | A61M 15/0028 |
| 2020/0170298 | A1 * | 6/2020 | Lee | A24F 40/46 |
| 2020/0275710 | A1 * | 9/2020 | Waller | A24F 42/60 |

FOREIGN PATENT DOCUMENTS

| | | | | |
|---|---|---|---|---|
| JP | H05-507637 | A | 11/1993 | |
| WO | WO 91/19524 | A2 | 12/1991 | |
| WO | WO 92/17233 | A1 | 10/1992 | |
| WO | WO 2019/159123 | A1 | 10/1992 | |
| WO | WO 2020/178715 | A1 | 8/2019 | |
| WO | WO-2020178714 | A1 * | 9/2020 | A24F 13/08 |

OTHER PUBLICATIONS

Bell et al., "Effects of Static on Plastics used in Drug Delivery Devices," *ONDrugDelivery magazine*, Dec. 2014;Issue 53: pp. 36-39.

"Asthma Inhaler Chamber" RTP Co. Imagineering Plastics, [online] printed May 19, 2023. https://www.rtpcompany.com/asthma-inhaler-chamber/, 4 pgs.

European Search Report for EP 20213327.8 issued by the European Patent Office on Jun. 1, 2021; 11 pgs.

International Search Report and Written Opinion for PCT/IB2021/061191, issued by the European Patent Office, Jan. 28, 2022; 13 pgs.

Marple et al., "Next generation pharmaceutical impactor (a new impactor for pharmaceutical inhaler testing). Part I: Design," *Journal of Aerosol Medicine*, 2003; 16(3):283-99.

Marple et al., "Next generation pharmaceutical impactor (a new impactor for pharmaceutical inhaler testing). Part II: Archival calibration," *Journal of Aerosol Medicine*, 2003; 16(3):301-324.

* cited by examiner

INHALER ARTICLE HOLDER WITH ELECTROSTATIC DISCHARGE

This application is the § 371 U.S. National Stage of International Application No. PCT/IB2021/061191, filed 1 Dec. 2021, which claims the benefit of European Application No. 20213327.8, filed 11 Dec. 2020, the disclosures of which are incorporated herein by reference.

The present disclosure relates to an inhaler article holder, the inhaler article holder includes an electrostatic discharge circuit when held by a consumer.

Dry powder inhalers are not always fully suitable to provide dry powder particles to the lungs at inhalation or air flow rates that are within conventional smoking regime inhalation or air flow rates. Dry powder inhalers may be complex to operate or may involve moving parts. Dry powder inhalers often strive to provide an entire dry powder dose or capsule load in a single breath.

Inhaler articles may retain capsules containing dry powder. These capsules may be activated by piercing an aperture though the capsule wall. A user puffs (draws or inhales) from the consumable mouthpiece side. This action forces air flow through the dry powder inhaler. It is generally known that drug delivery in dry powder and aerosol inhalers can be hindered by static attraction of the drug substance to surfaces along the drug flow path.

As the dry particles flow though the dry powder inhaler system, interactions between the particles and the surfaces encountered through the dry powder inhaler system cause electrostatic or static buildup. This electrostatic buildup causes dry particles to be attracted to each other and surfaces encountered through the dry powder inhaler system. This may result in adhesion of dry particles to surfaces encountered through the dry powder inhaler system. Dry powder adhesion or buildup on these surface degrade the operation of the dry powder inhaler. Dry powder adhesion or buildup on these surface increases the maintenance required to effectively operate the dry powder inhaler.

It is desirable to provide an electrical conducting pathway within a dry powder inhaler system to prevent or minimize electrostatic buildup within the dry powder flow path. It is desirable to provide an inhaler article holder that prevents or minimizes static electricity build-up and attraction of dry powder particles to the surfaces of the holder. It is desirable to effectively discharge any static electricity from the inhaler article holder during use to prevent accumulation of dry powder on the holder surfaces along the dry powder flow path.

According to an aspect of the present invention, there is provided an inhaler article holder comprising, a housing defining a housing cavity and an outer surface, and a sleeve positioned within the housing cavity. The sleeve is arranged to receive an inhaler article and the sleeve is movable within the housing cavity between a first position and a second position. A piercing element is arranged to pierce the inhaler article received within the sleeve when the sleeve is in the second position. The sleeve is electrically coupled to the housing to form a static electricity discharge circuit when the housing is electrically grounded.

Advantageously, providing a static electricity electrical pathway from the sleeve removes static electricity buildup at the sleeve and prevents or mitigates accumulation of dry powder on the sleeve surfaces. The reduced static electricity prevents or mitigates dry powder buildup to maintain clean device surfaces and reduce maintenance of the device. Reducing dry powder buildup in or on device surfaces provides more dry powder to the user, improving efficiency of the device. Utilizing antistatic materials for the sleeve and elements of the static electricity discharge circuit provides a simple and easy to assemble inhaler article holder.

This disclosure is directed to a holder for an inhaler article, referred to as an "inhaler article holder". The inhaler article holder includes a single offset piercing element. The inhaler article holder is configured to receive a consumable inhaler article, activate the capsule within the inhaler article by piercing the capsule, and induce swirling inhalation airflow into an inhaler article during consumption. The inhaler article holder and an inhaler article may form an inhaler system to which this disclosure is directed.

Portions of the inhaler article holder, specifically portions of the movable sleeve that receives the inhaler article, may come into contact with dry powder particles that are entrained in the inhalation airflow. For example, an airflow element forms a portion of the sleeve and the airflow element also extends into the sleeve lumen and into a received inhaler article. Applicant discovered that this airflow element was susceptible to dry powder buildup on its surfaces during consumption due to electrostatic attraction of the dry particles interacting with the electrical insulating airflow element.

Forming these sleeve portions to be antistatic and then electrically coupling these sleeve portions to the electrical conducting housing of the inhaler article holder forms an electrostatic discharge circuit when the user grounds the housing by contacting the housing during consumption of the inhaler article. Static electricity is then drawn away from the inhaler article holder surfaces interacting with the entrained dry powder particles during consumption. The reduces static electricity prevents or mitigates dry powder buildup to maintain clean devices surface and reduce maintenance of the device.

The inhaler article holder described herein may be combined with an inhaler article containing a capsule. The inhaler article may be used to activate the inhaler article by piercing the capsule, providing reliable activation of the capsule by puncturing the capsule with the piercing element of the inhaler article holder. Particles may be released from the capsule upon drawing or creating an airflow around the pierced capsule. The inhaler system thus delivers the dry powder particles to a consumer. The inhaler article holder is separate from the inhaler article, but the consumer utilizes both the inhaler article and the inhaler article holder while consuming the dry powder particles released within the inhaler article. A plurality of these inhaler articles may be combined with an inhaler article holder to form a system or kit. A single inhaler article holder may be utilized on 10 or more, or 25 or more, or 50 or more, or 100 or more, inhaler articles to activate (puncture or pierce) a capsule contained within each inhaler article and provide reliable activation. The inhaler article may optionally provide a visual indication (marking), for each inhaler article of the activation of the inhaler article.

The inhaler article has an airflow path. Airflow is introduced into the inhaler article by an inhalation (or puff) from a user. The inhaler article holder creates swirling inhalation airflow. This swirling inhalation airflow is introduced to the inhaler article. The distal end or upstream-most end of the inhaler article includes an open aperture that defines an open central passage of the open tubular element configured to receive swirling inhalation airflow.

The swirling inhalation airflow then continues downstream into the capsule cavity and induces rotation of a capsule in the capsule cavity. The activated capsule then releases a dose of particles into the swirling inhalation airflow downstream through the mouthpiece to the consumer. Thus, the swirling inhalation airflow is created upstream from the inhaler article and swirling inhalation airflow enters the distal end or upstream-most end of the inhaler article.

An inhaler article comprises an elongated tubular body extending along an inhaler longitudinal axis from a mouthpiece end to a distal end. The mouthpiece end is the proximal end, or the downstream end. The distal end is the upstream end. A capsule cavity is defined within the body bounded downstream by a filter element and bounded upstream by an open tubular element defining a central passage. Prior to insertion into an inhaler article holder, the distal end of the inhaler article may be closed. After insertion into an inhaler article holder, the distal end of the inhaler article may be open. The distal end of the inhaler article may interact with complimentary structures in the inhaler article holder so that, upon introducing the inhaler article into the inhaler article holder, the distal end of the inhaler article may open. When introduced into the inhaler article holder, the distal end of the inhaler article has a central passage which forms an open air-inlet aperture extending from the distal end of the body to the capsule cavity. A capsule is disposed within the capsule cavity, the central passage may have a smaller diameter then the capsule. Thus, the capsule may not pass through the central passage and is retained within the capsule cavity.

The inhaler article holder includes a housing comprising a housing cavity for receiving an inhaler article and a sleeve configured to retain an inhaler article within the housing cavity. The housing cavity is defined by a single housing opening that extends into the housing to a closed end along a housing longitudinal axis. The single housing opening is configured to receive the inhaler article. The housing is formed of an electrically conductive material. Preferably the housing is formed of a metal such as, for example, aluminium.

The sleeve is contained within the housing cavity and is movable along the housing longitudinal axis between a first position and a second position. The sleeve may be slidable along the housing longitudinal axis between a first position and a second position. In the first position the sleeve is located adjacent to the single housing opening. In the second position the sleeve is further away from the single housing opening a lateral distance along the longitudinal axis.

The sleeve extends from an open end to a closed end (or restricted end) and defines a cylindrical lumen along a longitudinal axis of the sleeve. The open end of the sleeve aligns with the single housing opening.

The sleeve closed end includes an airflow element and an aperture to allow the piercing element to pass through the closed end and extend into the sleeve lumen. The airflow element includes one or more inhalation air inlets that provide airflow communication from the annular space around the sleeve into the sleeve cylindrical lumen. This airflow element is configured to induce rotating or swirling inhalation airflow into the sleeve cylindrical lumen and directly into the inhaler article capsule cavity. This swirling or rotational inhalation airflow may be transmitted into an inhaler article to rotate a capsule and release dry powder contained within the capsule.

The airflow element of the sleeve includes a tubular element having a central passage in fluid communication with the sleeve cavity. The airflow element has at least one air inlet allowing inhalation air to enter into the central passage. The at least one air inlet extends in a direction that is tangential to the central passage to generate the swirling or rotational inhalation airflow.

The airflow element of the sleeve includes a tubular element having a central passage in fluid communication with the sleeve cavity. The airflow element has at least two air inlets allowing inhalation air to enter into the central passage. The at least two air inlets extend in a direction that is tangential to the central passage to generate the swirling or rotational inhalation airflow.

The airflow element of the sleeve includes a tubular element having a central passage in fluid communication with the sleeve cavity. The airflow element has at least three air inlets allowing inhalation air to enter into the central passage. The at least three air inlets extend in a direction that is tangential to the central passage to generate the swirling or rotational inhalation airflow.

The inhaler article holder may further include a piercing element fixed to and extending from a housing inner surface of the cavity. The piercing element is configured to extend through the closed end of the sleeve and into the sleeve cavity along a longitudinal axis of the housing. The piercing element contacts and pierces the capsule of a received inhaler article once the sleeve moves from the first position to the second position. Moving the sleeve from the second position to the first position removes the piercing element from the capsule and exposes an aperture in the capsule that allows dry particles contained within the capsule to be released from the capsule as inhalation air rotates the capsule. The piercing element is preferably electrically conductive. The piercing element is preferably formed of a metal.

The piercing element may electrically couple the sleeve with the housing. The piercing element may contact the sleeve at the airflow element. The airflow element may include an aperture to receive and allow the piercing element to pass through the airflow element.

The sleeve closed end may further include a sleeve bottom element substantially forming the closed end of the sleeve. The sleeve bottom element may be fixed and contact the airflow element. The sleeve bottom element may extend away from the airflow element a distance along the sleeve longitudinal axis and toward the closed end of the housing cavity. The sleeve bottom element may have an aperture that contains the piercing element and allows the piercing element to pass through the sleeve bottom element aperture.

The piercing element may contact the sleeve at the sleeve bottom element. The sleeve bottom element may electrically couple the sleeve or airflow element to the housing. The piercing element may electrically couple the sleeve with the housing via both the sleeve bottom element and the airflow element.

The inhaler article holder may further include a spring member configured to bias the sleeve away from the piercing element. The spring member may bias the sleeve away from the second position to the first position. The spring member may be in a relaxed state in the sleeve first position. The spring member may be in a compressed state in the second position. Preferably the piercing element is disposed within the spring member. The spring member is preferably electrically conductive. The spring member is preferably formed of a metal.

The spring member may electrically couple the sleeve with the housing. The spring member may contact the airflow element and electrically couple the sleeve or airflow element to the housing. The spring member may contact the sleeve bottom element and electrically couple the sleeve with the housing via both the sleeve bottom element and the airflow element.

The sleeve may include an elongated slot extending along a longitudinal length of the sleeve. The housing may further include a pin extending from an inner surface of the housing cavity. The pin may be configured to mate with the elongated slot to maintain alignment of the sleeve as it moved between the first and second positions.

An inner housing may be contained within the housing cavity. The inner housing may separate at least a portion of the sleeve from the inner surface of the housing cavity. The inner housing may separate a fixed end of the piercing element from the inner surface of the housing cavity. The inner housing may separate at the spring member from the inner surface of the housing cavity.

The inner housing may electrically couple the sleeve with the housing. The inner housing may contact the spring member and electrically couple the sleeve or airflow element to the housing. The inner housing may contact the piercing element and electrically couple the sleeve with the housing via both the sleeve bottom element and the airflow element.

The sleeve may have a surface resistivity less than $1\times10^{12}$ ohm/sq or less than $1\times10^{11}$ ohm/sq or less than $1\times10^{10}$ ohm/sq. The sleeve may be formed of a plastic material having a surface resistivity less than $1\times10^{12}$ ohm/sq or less than $1\times10^{11}$ ohm/sq or less than $1\times10^{10}$ ohm/sq.

The airflow element has a surface resistivity less than $1\times10^{12}$ ohm/sq or less than $1\times10^{11}$ ohm/sq or less than $1\times10^{10}$ ohm/sq. The airflow element may be formed of a plastic material having a surface resistivity less than $1\times10^{12}$ ohm/sq or less than $1\times10^{11}$ ohm/sq or less than $1\times10^{10}$ ohm/sq.

The sleeve bottom element has a surface resistivity less than $1\times10^{12}$ ohm/sq or less than $1\times10^{11}$ ohm/sq or less than $1\times10^{10}$ ohm/sq. The sleeve bottom element may be formed of a plastic material having a surface resistivity less than $1\times10^{12}$ ohm/sq or less than $1\times10^{11}$ ohm/sq or less than $1\times10^{10}$ ohm/sq.

The inner housing has a surface resistivity less than $1\times10^{12}$ ohm/sq or less than $1\times10^{11}$ ohm/sq or less than $1\times10^{10}$ ohm/sq. The inner housing may be formed of a plastic material having a surface resistivity less than $1\times10^{12}$ ohm/sq or less than $1\times10^{11}$ ohm/sq or less than $1\times10^{10}$ ohm/sq.

The phrase "surface resistivity" refers to a materials ability to discharge electrostatic loads. Surface resistivity is measured utilizing the standard method ASTM D 257 ESD STM11.11 IEC 60093. Surface resistivity is the resistance to leakage current along an insulating material's surface. Two parallel electrodes within a distance of each other equal to their contact length come in contact with the material's surface to measure surface resistivity. Therefore, the potential gradient's quotient (V/m) and current per unit of electrode length (A/m) represent the resistivity. The lengths in the surface resistivity and quotient cancel are generally measured in Ohms because the electrodes' four ends form a square. However, some test results use Ohms per square due to its more descriptive nature. Surface resistivity defines a fixed surface length's electrical resistance on an insulating material. This measurement does not take physical dimensions such as thickness and diameter into consideration. Since it only determines the surface's resistivity, only one physical measurement is required. Accordingly, surface resistivity is measured between electrodes along the insulator material's surface.

Plastic material typically has a surface resistivity greater than $1\times10^{12}$ ohm/sq. These plastic materials typically allow electrostatic forces to build up on the surface of these plastic materials. The built up electrostatic forces attract dry powder particles and adhere these dry powder particles to the surface of these plastic surfaces.

Antistatic materials have a surface resistivity less than $1\times10^{12}$ ohm/sq or less than $1\times10^{11}$ ohm/sq or less than $1\times10^{10}$ ohm/sq. Antistatic plastic materials are commercially available, for example from RTP Company (Winona, Minnesota, USA) under the trade designations RPT 399 X 155792 B NS Polycarbonate, RPT 2599 X 156311 NS Polycarbonate/ABS Alloy, RPT 1199 A X 155793 NS Polyethylene Terephthalate Glycol Modified PETG, or RPT 899 X 149765 B Acetal (POM).

Inhalable powders may include various active agents. The active agent may comprise an alkaloid such as nicotine or anatabine or anabasine, for example. Preferably, the active agent comprises solid salt of an alkaloid, such as a nicotine salt.

The amount of active agent may be selected based on the desired or intended use of the inhalable dry powder. For example, the amount of active agent may be between 0.5 wt-% and 10 wt-% of the total weight of the dry powder particles. The dry powder particles may comprises 0.5 wt-% or more, 1 wt-% or more, 2 wt-% or more, or 3 wt-% or more of the active agent, and 12 wt-% or less, 10 wt-% or less, 9 wt-% or less, 8 wt-% or less, or 7 wt-% or less, of the active agent, or from 0.5 wt-% to 10 wt-%, from 1 wt-% to 8 wt-%, from 1.5 wt-% to 6 wt-%, or from 2 wt-% to 5 wt-of the active agent.

The dry powder particles may comprises 0.5 wt-% or more, 1 wt-% or more, 2 wt-% or more, or 3 wt-% or more of nicotine, and 12 wt-% or less, 10 wt-% or less, 9 wt-% or less, 8 wt-% or less, or 7 wt-% or less, of nicotine, or from 0.5 wt-% to 10 wt-%, from 1 wt-% to 8 wt-%, from 1.5 wt-% to 6 wt-%, or from 2 wt-% to 5 wt-% nicotine.

The amount of active agent may also be selected on a per-dose basis. The inhalable powder may be packaged in a single dose form or in a multiple dose form. For example, the inhalable powder may comprise 0.5 mg or more, 1 mg or more, 2 mg or more, or 5 mg or more of the active agent per dose. The inhalable powder may comprise 500 mg or less, 200 mg or less, 100 mg or less, 50 mg or less, 20 mg or less, or 10 mg or less of the active agent per dose. In some embodiments, the inhalable powder comprises from 0.01 to 10 mg of anatabine or nicotine or anabasine per dose, 0.05 to 5 mg anatabine or nicotine or anabasine per dose, or 0.1 to 1 mg of anatabine or nicotine or anabasine per dose.

In embodiments, the capsule contains from 1 to 20 doses. In embodiments, the capsule contains from 1 to 10 doses. In embodiments the capsule contains from 10 to 20 doses. In embodiments, the capsule contains 1 dose. In embodiments, the capsule contains 2 doses. In embodiments, the capsule contains 3 doses. In embodiments, the capsule contains 4 doses. In embodiments, the capsule contains 5 doses. In embodiments, the capsule contains 6 doses. In embodiments, the capsule contains 7 doses. In embodiments, the capsule contains 8 doses. In embodiments, the capsule contains 9 doses. In embodiments, the capsule contains 10 doses. In embodiments, the capsule contains 11 doses. In embodiments, the capsule contains 12 doses. In embodiments, the capsule contains 13 doses. In embodiments, the capsule contains 14 doses. In embodiments, the capsule contains 15 doses. In embodiments, the capsule contains 16 doses. In embodiments, the capsule contains 17 doses. In embodiments, the capsule contains 18 doses. In embodiments, the capsule contains 19 doses. In embodiments, the capsule contains 20 doses.

The dry powder particles may have a particle size of 20 μm or less, 10 μm or less, or 5 μm or less, or 0.1 μm or greater, 0.2 μm or greater, or 0.5 μm or greater, or ranging from 0.5 μm to 10 μm, or from 0.75 μm to 5 μm, or from 1 μm to 5 μm, or from 1 μm to 3 μm, or from 1.5 μm to 2.5 μm. The desired particle size range may be achieved by spray drying, milling, sieving, or a combination thereof.

The dry powder particles may be further mixed with a second population of particles to form a powder system. Preferably, the second population of particles have a different particle size or larger particle size than the dry powder particles. For example, the second population of particles may have a particle size of about 20 μm or greater, or about 50 μm or greater, 200 μm or smaller, 150 μm or smaller, or in a range from 50 μm to 200 μm, or from 50 μm to 150 μm. The second population of particles may have any useful size distribution for inhalation delivery selectively into the mouth or buccal cavity of a user. The larger second population of flavourant particles may assist in delivery of the dry powder particles to the inhalation airflow to the user.

The dry powder particles and second population of particles may be combined in any useful relative amount so that the second population of particles are detected by the user when consumed with the dry powder particles. Preferably, the dry powder particles and second population of particles form at least about 90 wt-% or at least about 95 wt-% or at least about 99 wt-% or 100 wt-% of the total weight of the powder system.

The dry powder particles may be mixed with a second population of flavourant particles to form a powder system. Preferably, the second population of flavourant particles have a different particle size or larger particle size than the dry powder particles. For example, the flavor particles may have a particle size of about 20 μm or greater, or about 50 μm or greater, 200 μm or smaller, 150 μm or smaller, or in a range from 50 μm to 200 μm, or from 50 μm to 150 μm. The second population of flavourant particles may have any useful size distribution for inhalation delivery selectively into the mouth or buccal cavity of a user. The larger second population of flavourant particles may assist in delivery of the dry powder particles to the inhalation airflow to the user.

The dry powder particles and second population of flavourant particles may be combined in any useful relative amount so that the second population of flavourant particles are detected by the user when consumed with the dry powder particles. Preferably, the dry powder particles and second population of flavourant particles form at least about 90 wt-% or at least about 95 wt-% or at least about 99 wt-% or 100 wt-% of the total weight of the powder system.

The dry powder particles or powder system may be provided in a suitable dosage form. For example, the dry powder particles or powder system may be provided in a capsule. The dosage form (for example, capsule) may be configured for use in a suitable inhaler. For example, the capsule may be utilized in an inhaler device having a capsule cavity. Air flow management through a capsule cavity of the inhaler device may cause a capsule contained therein to rotate during inhalation and consumption. The capsule may contain dry powder particles or powder system.

The term "particle size" is used here to refer to the mass median aerodynamic diameter (MMAD) of the particle or set of particles, unless otherwise stated. Such values are based on the distribution of the aerodynamic particle diameters defined as the diameter of a sphere with a density of 1 gm/cm$^3$ that has the same aerodynamic behavior as the particle which is being characterized.

In particular for a powder system reference is commonly made to the mass median aerodynamic diameter (MMAD), one of the metrics most widely adopted as a single number descriptor of aerodynamic particle-size distribution. The MMAD is a statistically derived figure for a particle sample: by way of example, an MMAD of 5 micrometres means that 50 percent of the total sample mass will be present in particles having aerodynamic diameters of less than 5 micrometres, and that the remaining 50 percent of the total sample mass will be present in particles having an aerodynamic diameter greater than 5 micrometres. In the context of the present invention, when describing a powder system, the term "particle size" preferably refers to the MMAD of the powder system.

The MMAD of a powder system is preferably measured with a cascade impactor. Cascade impactors are instruments which have been extensively used for sampling and separating airborne particles for determining the aerodynamic size classification of aerosol particles. In practice, cascade impactors separate an incoming sample into discrete fractions on the basis of particle inertia, which is a function of particle size, density and velocity. A cascade impactor typically comprises a series of stages, each of which comprises a plate with a specific nozzle arrangement and a collection surface. As nozzle size and total nozzle area both decrease with increasing stage number, the velocity of the sample-laden air increases as it proceeds through the instrument. At each stage, particles with sufficient inertia break free from the prevailing air stream to impact on the collection surface. Therefore, at any given flow rate, each stage is associated with a cut-off diameter, a figure that defines the size of particles collected. With increasing stage number, velocity increases and so stage cut-off diameter decreases. Thus, the cut-off diameter associated with a given stage is a function of the air-flow rate used for testing. To reflect in-use performance, nebulisers are routinely tested at 15 L/min and dry powder inhalers may be tested at flow rates up to 100 L/min.

Preferably, in the context of the present invention, the MMAD of a powder system is measured with a Next Generation Impactor (NGI) 170 (available from Copley Scientific AG). The NGI is a high performance, precision, particle classifying cascade impactor having seven stages plus a Micro-Orifice Collector (MOC). Characteristics and operation principle of a NGI are described, for example, in Marple et al., Journal of Aerosol Medicine—Volume 16, Number 3 (2003). More preferably, measurements are carried out at 20±3 degrees Celsius and relative humidity of 35±5 percent.

A dry powder formulation typically contains less than or equal to about 15 percent by weight moisture, preferably less than or equal to about 10 percent moisture, even more preferably less than or equal to about 6 percent by weight moisture. Most preferably a dry powder formulation contains less than or equal to about 5 percent by weight moisture or even less than or equal to about 3 percent by weight moisture or even less than or equal to about 1 percent by weight moisture.

All values reported as a percentage are presumed to be weight percent based on the total weight.

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

The term "substantially" as used here has the same meaning as "significantly," and can be understood to modify the relevant term by at least about 90%, at least about 95%, or at least about 98%. The term "not substantially" as used here has the same meaning as "not significantly," and can be understood to have the inverse meaning of "substantially," i.e., modifying the relevant term by not more than 10%, not more than 5%, or not more than 2%.

The invention is defined in the claims. However, below there is provided a non-exhaustive listing of non-limiting examples. Any one or more of the features of these examples may be combined with any one or more features of another example, embodiment, or aspect described herein.

Example Ex1. An inhaler article holder comprising, a housing defining a housing cavity and an outer surface, and a sleeve positioned within the housing cavity. The sleeve is arranged to receive an inhaler article and the sleeve is movable within the housing cavity between a first position and a second position. A piercing element is arranged to pierce the inhaler article received within the sleeve when the sleeve is in the second position. The sleeve is electrically coupled to the housing to form a static electricity discharge circuit when the housing is electrically grounded.

Example Ex2. The inhaler article holder of Ex1, further comprising a spring member contacting a portion of the sleeve, and the spring member electrically coupling the sleeve with the housing.

Example Ex3. The inhaler article holder of any preceding Example, wherein the piercing element electrically couples the sleeve with the housing.

Example Ex4. The inhaler article holder of Examples Ex2 or Ex3, wherein the piercing element is disposed within the spring member.

Example Ex5. The inhaler article holder of any preceding Example, wherein the piercing element is disposed within the sleeve when the sleeve is in the second position.

Example Ex6. The inhaler article holder of any preceding Example, wherein the housing is formed of a metal.

Example Ex7. The inhaler article holder of any preceding Example, wherein the piercing element is formed of a metal.

Example Ex8. The inhaler article holder of Example Ex2 to Ex7, wherein the spring member is formed of a metal.

Example Ex9. The inhaler article holder of any preceding Example, wherein the sleeve is formed of a polymer having a surface resistivity less than $1\times10^{11}$ ohm/sq or less than $1\times10^{10}$ ohm/sq. (ASTM D 257 ESD STM11.11 IEC 60093)

Example Ex10. The inhaler article holder of any preceding Example, wherein the sleeve comprises an airflow element having two or more airflow inlets configured to form swirling airflow into the sleeve, and the airflow element is electrically coupled to the housing.

Example Ex11. The inhaler article holder of Ex10, wherein the airflow element is formed of a polymer having a surface resistivity less than $1\times10^{11}$ ohm/sq or less than $1\times10^{10}$ ohm/sq.

Example Ex12. The inhaler article holder of Ex11, wherein the sleeve extends from an open end to a closed end and defines a cylindrical lumen for receiving an inhaler article, the open end of the sleeve being aligned with an opening in the housing for receiving an inhaler article.

Example Ex13. The inhaler article holder of Ex12, wherein the sleeve closed end comprises a sleeve bottom element substantially closing the sleeve at the closed end, and the airflow element is coupled to the sleeve bottom element, and the air flow element extending from the sleeve bottom element and into the sleeve cylindrical lumen, and the airflow element is electrically coupled to the housing through the sleeve bottom element and spring member or piercing element.

Example Ex14. The inhaler article holder of Ex12, wherein the sleeve extends from an open end to a closed end and defines a cylindrical lumen for receiving an inhaler article, the open end of the sleeve being aligned with an opening in the housing for receiving an inhaler article, the sleeve closed end comprises a sleeve bottom element substantially closing the sleeve at the closed end and the airflow element is coupled to the sleeve bottom element and extends away from the sleeve bottom element and into the sleeve cylindrical lumen, and the airflow element is electrically coupled to the housing through the sleeve bottom element and spring member or piercing element.

Example Ex15. The inhaler article holder of Ex13 or Ex14, wherein the sleeve bottom element is formed a polymer having a surface resistivity less than $1\times10^{11}$ ohm/sq or less than $1\times10^{10}$ ohm/sq.

Example Ex16. The inhaler article holder of any preceding Example, further comprising an inner housing formed of a polymer having a surface resistivity less than $1\times10^{11}$ ohm/sq or less than $1\times10^{10}$ ohm/sq, and the inner housing electrically couples the spring member to the housing.

Example Ex17. The inhaler article holder of Ex16, wherein the inner housing electrically couples the piercing element to the housing.

Example Ex18. The inhaler article holder of any preceding Example, wherein the housing is grounded to a user contacting the housing outer surface.

Example Ex19. The inhaler article holder of any preceding Example, wherein each of the static electricity discharge circuit elements have a surface resistivity less than $1\times10^{11}$ ohm/sq or less than $1\times10^{10}$ ohm/sq.

Example Ex20. The inhaler article holder of Ex12, wherein the opening in the housing receives the inhaler article and defines an air inlet into the housing and provide inhalation air through the airflow element into the sleeve cylindrical lumen.

Example Ex21. An inhaler system comprising, the inhaler article holder according to any preceding Example and an inhaler article containing a capsule disposed within a capsule cavity of the inhaler article. The capsule containing pharmaceutically active particles comprising nicotine, the pharmaceutically active particles having a mass median aerodynamic diameter of about 5 micrometres or less, or in a range from about 0.5 micrometres to about 4 micrometres, or in a range from about 1 micrometres to about 3 micrometres.

Example Ex22. The system according to Ex21, wherein the capsule further contains a second population of flavour particles having a mass median aerodynamic diameter of about 20 micrometres or greater, or about 50 micrometres or greater, or in a range from about 50 to about 200 micrometres, or from about 50 to about 150 micrometres.

The Examples will now be further described with reference to the figures in which.

Figure 1:
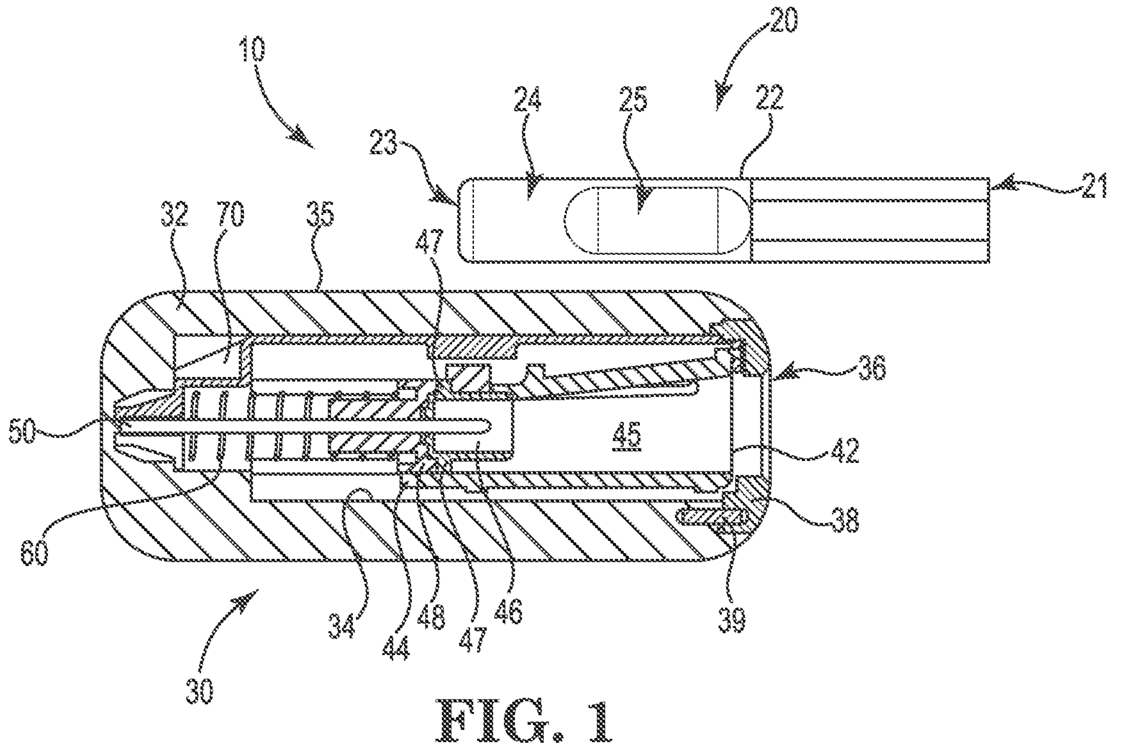
FIG. 1 is a schematic cross-sectional diagram of an illustrative inhaler system.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Figure 2:
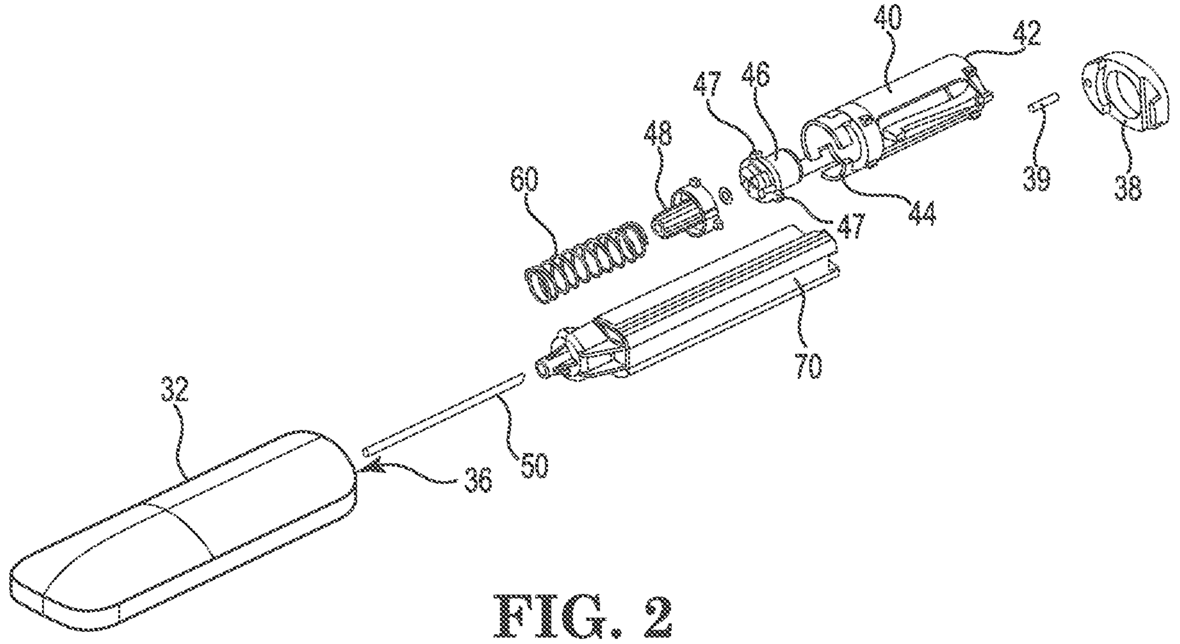
FIG. 2 is perspective exploded view of an illustrative inhaler article holder.
Figure 3A:
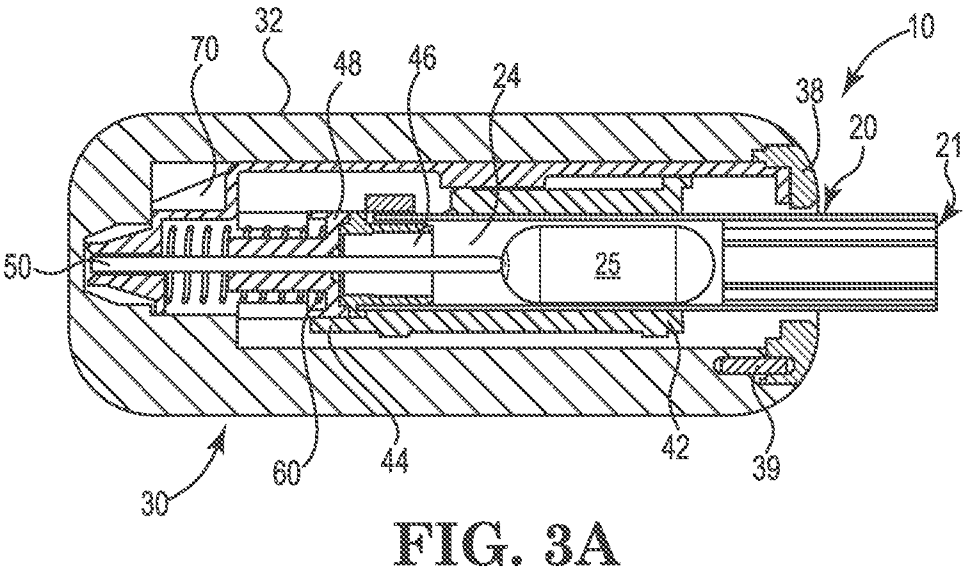
FIG. 3A is a schematic cross-sectional diagram of an illustrative inhaler system where the inhaler article is received in the inhaler article holder and piercing the capsule in a second position.
Figure 3B:
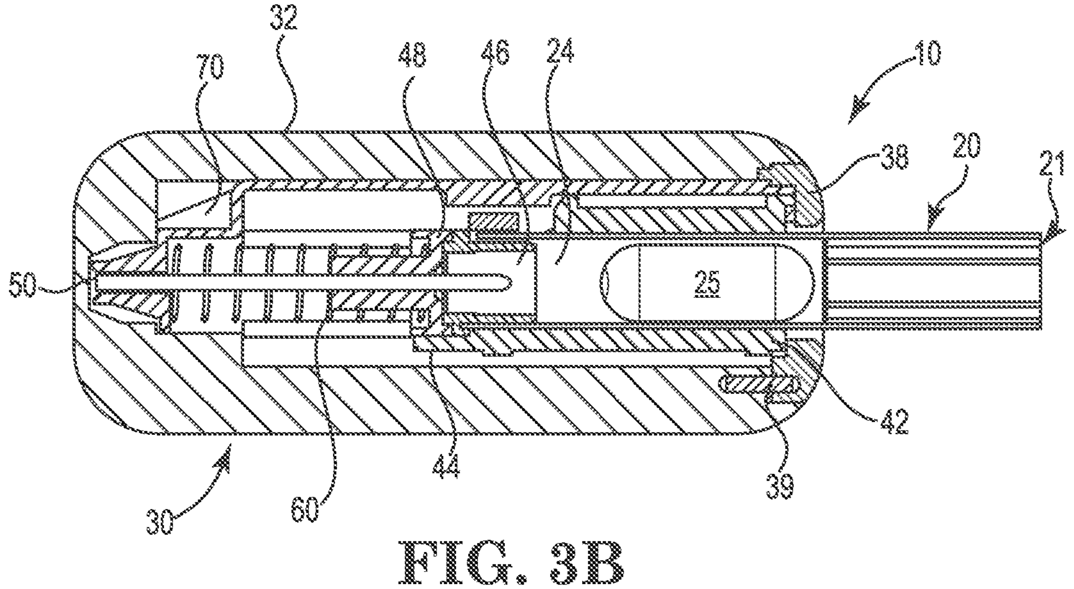
FIG. 3B is a schematic cross-sectional diagram of the illustrative inhaler system of FIG. 3A where the piercing element is retracted from the capsule in a first position.
Figure 4:
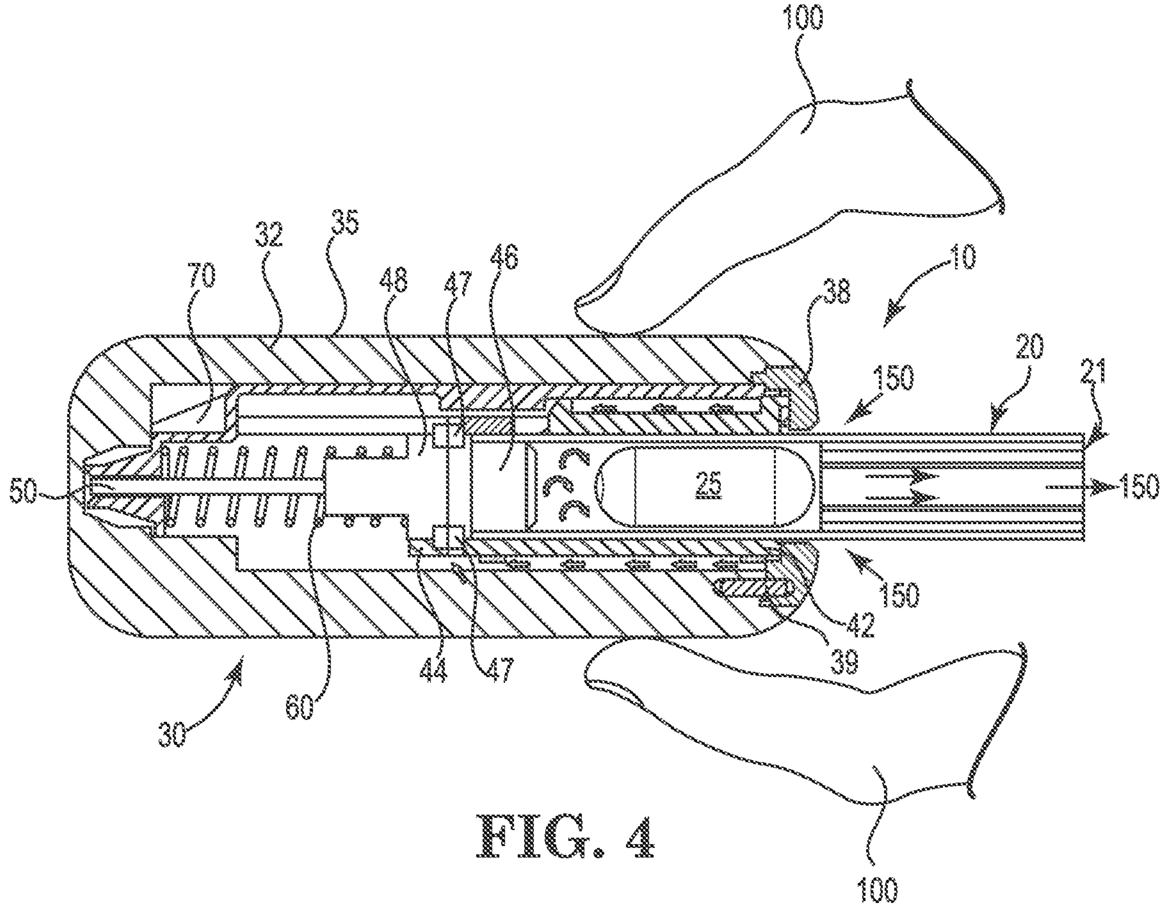
FIG. 4 is another schematic cross-sectional diagram of FIG. 3B illustrating the inhalation airflow path through the inhaler system.

FIG. 1 is a schematic cross-sectional diagram of an illustrative inhaler system 10. FIG. 2 is perspective exploded view of an illustrative inhaler article holder 30. FIG. 3A is a schematic cross-sectional diagram of an illustrative inhaler system 10 where the inhaler article 20 is received in the inhaler article holder 30 and piercing the capsule 25 in a second or compressed position. FIG. 3B is a schematic cross-sectional diagram of the illustrative inhaler system 10 of FIG. 3A where the piercing element 50 is retracted from the capsule 25 in a first or relaxed position. FIG. 4 is another schematic cross-sectional diagram of FIG. 3B illustrating the inhalation airflow 150 path (arrows) through the inhaler system 10.

The inhaler article holder 30 is configured to receive a separate consumable inhaler article 20 and induce swirling inhalation airflow into and through an inhaler article 20 during consumption. The inhaler article holder 30 and an inhaler article 20 form an inhaler system 10. The inhaler article 20 remains in the inhaler article holder 30 during use by the consumer. The inhaler article holder 30 is configured to induce swirling inhalation airflow entering the received inhaler article 20.

The illustrative inhaler article 20 includes a body 22 extending from a mouthpiece end 21 to a distal end 23. A capsule cavity 24 is defined within the body 22. A capsule 25 is contained within the capsule cavity 24. Dry powder particles described above may be contained within the capsule 25. The capsule 25 may be pierced to form an aperture through the body of the capsule 25 and inhalation air may flow through the inhaler article 20 to release dry powder particles from the pierced capsule 25 and into the inhalation airflow and out of the mouthpiece end 21.

The inhaler article holder 30 includes a housing 32 defining a housing cavity defined by a housing inner surface 34, and an outer surface 35. A sleeve 40 is positioned within the housing cavity. The sleeve 40 is arranged to receive an inhaler article 20 and the sleeve 40 is movable within the housing cavity between a first position and a second position, along a longitudinal axis of the housing cavity.

A piercing element 50 is arranged to pierce the capsule 25 within the inhaler article 20 received within the sleeve 40 when the sleeve 40 is in the second position as illustrated in FIG. 3A. The sleeve 40 is electrically coupled to the housing 32 to form a static electricity discharge circuit when the housing 32 is electrically grounded, for example, when grasped by a user during inhalation.

The piercing element 50 may be configured to extend into the sleeve 40 along a longitudinal axis of the housing 32. The inhaler article holder 30 may include a spring member 60 configured to bias the sleeve 40 and any received inhaler article 20 away from the piercing element 50.

The sleeve 40 extends from an open end 42 to a closed end 44 (or restricted end) and defines a sleeve cavity 45 or cylindrical lumen 45 along a longitudinal axis of the sleeve 40. The open end 42 of the sleeve aligns with the single housing opening 36.

The sleeve closed end 44 includes an airflow element 46 and an aperture to allow the piercing element to pass through the closed end 44 and extend into the sleeve cavity 45. The airflow element 46 includes one or more inhalation air inlets 47 that provide airflow communication from the annular space around the sleeve 40 into the sleeve cylindrical lumen 45. This airflow element 46 is configured to induce rotating or swirling inhalation airflow into the sleeve cylindrical lumen 45 and directly into the inhaler article capsule cavity 24. This swirling or rotational inhalation airflow may be transmitted into an inhaler article 20 to rotate a capsule 25 and release dry powder contained within the capsule 25.

The airflow element 46 of the sleeve 40 includes a tubular element having a central passage in fluid communication with the sleeve cavity 45. The airflow element 46 has at least one air inlet 47 allowing inhalation air 150 to enter into the central passage. The at least one air inlet 47 extends in a direction that is tangential to the central passage to generate the swirling or rotational inhalation airflow.

The sleeve 40 includes a tubular element that may extend into the sleeve cavity 45 about 5 mm and have an outer diameter of about 5.5 mm and an inner diameter of about 4 mm. The received inhaler article 20 open distal end 23 may have an inner diameter of about 5.5 mm to provide an interference fit with the airflow element 46 tubular element.

The sleeve closed end 44 may further include a sleeve bottom element 48 substantially forming the closed end of the sleeve 40. The sleeve bottom element 48 may be fixed and contact the airflow element 46. The sleeve bottom element 48 may extend away from the airflow element 46 a distance along the sleeve longitudinal axis and toward the closed end of the housing cavity. The sleeve bottom element 48 may have an aperture that contains the piercing element 50 and allows the piercing element 50 to pass through the sleeve bottom element 48 aperture.

An inner housing 70 may be contained within the housing cavity. The inner housing 70 may separate at least a portion of the sleeve 40 from the inner surface of the housing cavity. The inner housing 70 may separate a fixed end of the piercing element 50 from the inner surface of the housing cavity. The inner housing 70 may separate the spring member 60 from the inner surface of the housing cavity.

An annular cover 38 may secure the inner housing 70 and sleeve 40 into the housing cavity. The annular cover 38 defines the single housing opening 36 for receiving the inhaler article 20. The annular cover 38 may be fixed to the housing 32 with a pin element 39.

FIG. 4 illustrates the inhalation airflow 150 path through the inhaler system 10. Inhalation airflow 150 enters the inhaler article holder 30 along the outer surface of the received inhaler article 20 and the annular cover 38. Once inside the housing cavity, the inhalation air 150 travels along the sleeve 40 length to the closed end 44 of the sleeve 40. The inhalation air 150 then enters the air inlet 47 of the airflow element 46 and forms swirling or rotating inhalation airflow 150 within the sleeve lumen 45. This swirling or rotating inhalation air is then directly transmitted into the distal end 23 of the inhaler article 20 and into the capsule cavity 24. The swirling inhalation airflow rotates or agitates the capsule 25 and dry powder particles are entrained in the inhalation airflow. The entrained inhalation airflow then flows out of the inhaler article via the mouthpiece end 21 and to the user 100. The inhalation airflow 150 path is illustrated in FIG. 4 with arrows.

Figure 5:
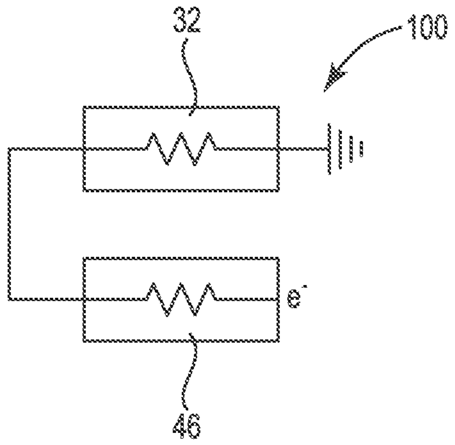
FIG. 5 is a schematic circuit diagram of an illustrative inhaler article holder.
Figure 6:
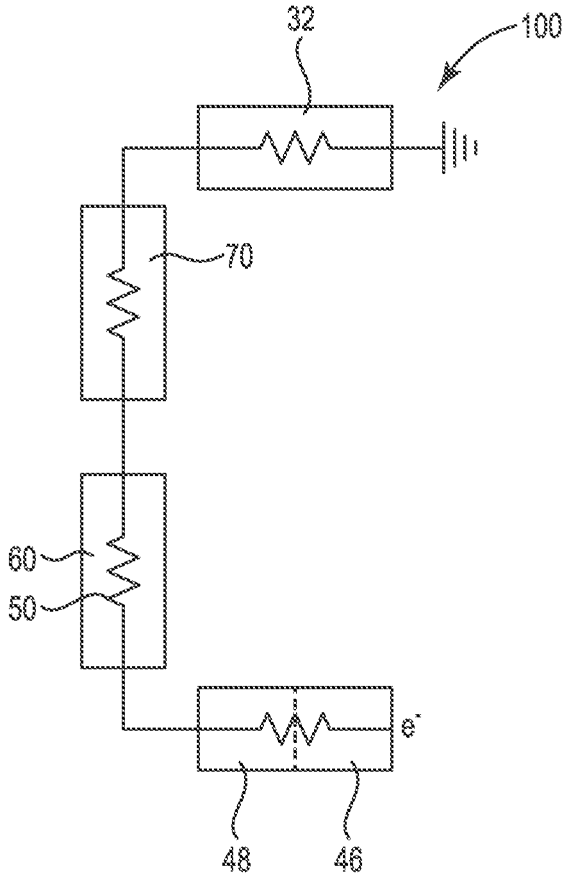
FIG. 6 is another schematic circuit diagram of an illustrative inhaler article holder.

FIG. 5 is a schematic circuit diagram of an illustrative inhaler article holder. FIG. 6 is another schematic circuit diagram of an illustrative inhaler article holder.

In FIG. 5 the circuit includes the sleeve or airflow element 46 is electrically coupled to the housing 32 and the housing 32 is grounded via a user 100 contacting the housing 32. Electrostatic forces $e^-$ conduct through the sleeve or airflow element 46 to the housing and then to ground, effectively minimizing electrostatic forces $e^-$ on the surface of the sleeve or airflow element 46.

In FIG. 6 the circuit includes the airflow element 46 is electrically coupled to the housing 32 and the housing 32 is grounded via a user 100 contacting the housing 32. Electrostatic forces $e^-$ conduct through the airflow element 46 to a sleeve bottom element 48 then to a spring member 60 or piercing element 50 and then to the inner housing 70 and then to the housing 32 and then to ground, effectively minimizing electrostatic forces $e^-$ on the surface of the airflow element 46.

For the purpose of the present description and of the appended claims, except where otherwise indicated, all numbers expressing amounts, quantities, percentages, and so forth, are to be understood as being modified in all instances by the term "about." Also, all ranges include the maximum and minimum points disclosed and include any intermediate ranges therein, which may or may not be specifically enumerated herein. In this context, therefore, a number A is understood as A ±2% of A. Within this context, a number A may be considered to include numerical values that are within general standard error for the measurement of the property that the number A modifies. The number A, in some instances as used in the appended claims, may deviate by the percentages enumerated above provided that the amount by which A deviates does not materially affect the basic and novel characteristic(s) of the claimed invention. Also, all ranges include the maximum and minimum points disclosed and include any intermediate ranges therein, which may or may not be specifically enumerated herein.

The invention claimed is:

1. An inhaler article holder comprising:

a housing defining a housing cavity and an outer surface;

a sleeve positioned within the housing cavity, wherein the sleeve is arranged to receive an inhaler article containing a capsule disposed within a capsule cavity of the inhaler article and the sleeve is movable within the housing cavity between a first position and a second position, wherein a portion of the sleeve extends into an interior of the inhaler article; and a piercing element arranged to pierce the inhaler article received within the sleeve when the sleeve is in the second position;

wherein the sleeve is electrically coupled to the housing and is configured to form a static electricity discharge circuit when the housing is electrically grounded.

2. The inhaler article holder according to claim 1, further comprising a spring member contacting a portion of the sleeve, and the spring member electrically coupling the sleeve with the housing.

3. The inhaler article holder according to claim 1, wherein the piercing element electrically couples the sleeve with the housing.

4. The inhaler article holder according to claim 2, wherein the piercing element is disposed within the spring member.

5. The inhaler article holder according to claim 1, wherein the housing is formed of a metal.

6. The inhaler article holder according to claim 1, wherein the sleeve is formed of a polymer having a surface resistivity less than $1\times10^{11}$ ohm/sq.

7. The inhaler article holder according to claim 1, wherein the sleeve comprises an airflow element configured to form swirling airflow, and the airflow element is electrically coupled to the housing.

8. The inhaler article holder according to claim 7, wherein the airflow element is formed of a polymer having a surface resistivity less than $1\times10^{11}$ ohm/sq.

9. The inhaler article holder according to claim 8, wherein the sleeve extends from an open end to a closed end and defines a cylindrical lumen for receiving an inhaler article, the open end of the sleeve is aligned with an opening in the housing for receiving an inhaler article, the closed end of the sleeve comprises a sleeve bottom element substantially closing the sleeve at the closed end, and the airflow element is coupled to the sleeve bottom element, and the airflow element extends away from the sleeve bottom element and into the cylindrical lumen of the sleeve, and the airflow element is electrically coupled to the housing through the sleeve bottom element and spring member or piercing element.

10. The inhaler article holder according to claim 9, wherein the sleeve bottom element is formed of a polymer having a surface resistivity less than $1\times10^{11}$ ohm/sq.

11. The inhaler article holder according to claim 2, further comprising an inner housing formed of a polymer having a surface resistivity less than $1\times10^{11}$ ohm/sq, and the inner housing electrically couples the spring member to the housing.

12. The inhaler article holder according to claim 1, wherein the housing is configured to be grounded to a user contacting the outer surface of the housing.

13. The inhaler article holder according to claim 11, wherein the inner housing electrically couples the piercing element to the housing.

14. An inhaler system comprising, the inhaler article holder according to claim 1, and the inhaler article containing the capsule disposed within the capsule cavity of the inhaler article, the capsule containing pharmaceutically active particles comprising nicotine, the pharmaceutically active particles having a mass median aerodynamic diameter of about 5 micrometres or less.

15. The inhaler system according to claim 14, wherein the capsule further contains a second population of flavour particles having a mass median aerodynamic diameter of about 50 micrometres or greaters.

16. The inhaler article holder according to claim 2, wherein the piercing element electrically couples the sleeve with the housing.

17. The inhaler article holder according to claim 7, wherein the sleeve is formed of a polymer having a surface resistivity less than $1\times10^{10}$ ohm/sq.

18. The inhaler article holder according to claim 4, wherein the sleeve is formed of a polymer having a surface resistivity less than $1\times10^{10}$ ohm/sq.

19. The inhaler article holder according to claim 18, further comprising an inner housing formed of a polymer having a surface resistivity less than $1\times10^{10}$ ohm/sq, and the inner housing electrically couples the spring member to the housing.

20. An inhaler system comprising, the inhaler article holder according to claim 1, and the inhaler article containing the capsule disposed within the capsule cavity of the inhaler article, the capsule containing pharmaceutically active particles comprising nicotine, the pharmaceutically active particles having a mass median aerodynamic diameter in a range from about 0.5 micrometres to about 4 micrometres, and the capsule further containing a second population of flavour particles having a mass median aerodynamic diameter in a range from about 50 to about 200 micrometres.

* * * * *